United States Patent [19]

Goldwasser et al.

[11] Patent Number: 4,558,005
[45] Date of Patent: Dec. 10, 1985

[54] MONOCLONAL ANTI-ERYTHROPOIETIN

[75] Inventors: Eugene Goldwasser; Clifford Kavinsky; Tania L. Weiss, all of Chicago, Ill.

[73] Assignee: University Patents, Inc., Westport, Conn.

[21] Appl. No.: 417,429

[22] Filed: Sep. 13, 1982

[51] Int. Cl.[4] .................................. G01N 33/; 54 C12P 21/00; C12N 5/00; C12N 5/02; A61K 39/00; A61K 35/14; A61K 37/00

[52] U.S. Cl. ............................... 435/7; 435/68; 435/240; 435/241; 435/188; 435/948; 424/85; 424/101; 436/500; 436/531; 436/548; 514/6; 260/112 B; 260/112 R

[58] Field of Search .............. 436/548, 500, 531; 260/112 B, 112 R; 424/85, 101, 88, 99; 435/7, 188, 68, 240, 241

[56] References Cited

U.S. PATENT DOCUMENTS

| | | | |
|---|---|---|---|
| 3,033,753 | 5/1962 | White et al. | 16.7/74 |
| 3,865,801 | 2/1975 | Chiba et al. | 260/112 R |
| 4,254,095 | 3/1981 | Fisher et al. | 424/1 |
| 4,361,509 | 11/1982 | Zimmerman et al. | 260/112 B |
| 4,465,624 | 8/1984 | Chiba et al. | 260/112 R |

OTHER PUBLICATIONS

Sevier et al., Clin. Chem. vol. 27, No. 11, pp. 1797–1806, 1981, "Monoclonal Antibodies in Clinical Immunology".
Davidson and Parish, J. Imm. Methods, 7: 291–295, (1975).
Gavey et al., eds., Methods in Immunology, 2nd ed., pp. 246–260, Massachusetts: W. A. Benjamin, Inc. (1970).
Goldwasser et al., "An Assay for Erythropoietin in Vitro at the Milliunit Level," Endocrinology, 97(2): 315–323, (Aug. 1975).
Kennett et al., eds., Monoclonal Antibodies, Hybridomas: A New Dimension in Biological Analyses, p. 405, New York: Plenum Press (1980).
Kohler and Milstein, Nature (London), 256: 495–497, (1975).
Kohler and Milstein, Eur. J. Imm., 6: 511–519, (1976).
Miyake et al., "Purification of Human Erythropoietin", J. Biol. Chem., 252(15): 5558–5564 (Aug. 10, 1977).
Reid, Methods in Enzymology, 58: 152–164; Jakoby and Pastan, eds., New York: Academic Press (1979).
Sherwood et al., "A Radioimmunoassay for Erythropoietin," Blood, 54(4): 885–893, (Oct. 1979).
Lee-Huang, "Monoclonal Antibodies to Human Erythropoietin", Fed. Proc., 41: 520 (1982).
Weiss et al., PNAS (USA), 79: 5465–5469, (1982).

Primary Examiner—Alvin E. Tanenholtz
Assistant Examiner—Robin Lyn Teskin
Attorney, Agent, or Firm—Marshall, O'Toole, Gerstein, Murray & Bicknell

[57] ABSTRACT

Hybridoma tumor cell line (ATCC Number CRL 8164). A monoclonal anti-erythropoietin antibody substance, Epoclonalan, produced by said cell line. Use of Epoclonalan in immonological methods for isolation of natural erythropoietin and for quantitative detection of erythropoietin in fluid samples.

10 Claims, No Drawings

MONOCLONAL ANTI-ERYTHROPOIETIN

BACKGROUND OF THE INVENTION

The present invention relates generally to materials and methods for use in immunological procedures for quantitative detection and isolation of the hormone erythropoietin in fluid samples. More specifically, the invention relates to a monoclonal anti-erythropoietin antibody, Epoclonalan, produced by a novel tumor cell line ATCC CRL 8164 and to uses of Epoclonalan in diagnostic assays on human fluids and in procedures for obtaining large quantities of, and characterizing human erythropoietin.

Erythropoiesis, the production of red blood cells, occurs continuously throughout the human life span to offset cell destruction. Erythropoiesis is a very precisely controlled physiological mechanism enabling sufficient numbers of red blood cells to be available in the blood for proper tissue oxygenation, but not so many that the cells would impede circulation. The formation of red blood cells occurs in the bone marrow and is under the control of the hormone, erythropoietin.

Erythropoietin, an acidic glycoprotein of approximately 34,000 molecular weight, may occur in three forms: $\alpha$, $\beta$, and asialo. The $\alpha$ and $\beta$ forms differ slightly in carbohydrate components, but have the same potency, biological activity and molecular weight. The asialo form is an $\alpha$ or $\beta$ form with the terminal carbohydrate (sialic acid) removed. Erythropoietin is present in very low concentrations in plasma when the body is in a healthy state wherein tissues receive sufficient oxygenation from the existing number of erythrocytes. This normal low concentration is enough to stimulate replacement of red blood cells which are lost normally through aging.

The amount of erythropoietin in the circulation is increased under conditions of hypoxia when the number of red blood cells in the circulation is reduced. Hypoxia may be caused by loss of large amounts of blood through hemorrhage, destruction of red blood cells by over-exposure to radiation, reduction in oxygen intake due to high altitudes or prolonged unconsciousness, or various forms of anemia. In response to tissues undergoing hypoxic stress, erythropoietin will increase red blood cell production by stimulating the conversion of primitive precursor cells in the bone marrow into pro-erythroblasts, bone marrow cells which subsequently mature, synthesize hemoglobin and are released into the circulation as red blood cells. When the number of red blood cells in circulation is greater than needed for normal tissue oxygen requirements, erythropoietin in circulation is decreased.

Because erythropoietin is essential in the process of red blood cell formation, the hormone has potential useful application in both the diagnosis and the treatment of blood disorders characterized by low or defective red blood cell production. Prior attempts to obtain erythropoietin in good yield from plasma or urine, however, have proven relatively unsuccessful. Complicated and sophisticated laboratory techniques are necessary and generally result in the collection of very small amounts of impure and unstable extracts containing erythropoietin.

U.S. Pat. No. 3,033,753 describes a method for partially purifying erythropoietin from sheep blood plasma. After injecting phenyl hydrazine hydrochloride into sheep in an amount sufficient to produce severe anemia, the blood is withdrawn and centrifuged to separate the plasma from the red cell portion. The plasma is then dialysed and brought into contact with an anion exchange resin. This eluate is further dialysed and lyophilized and introduced to two cation exchange resins. A suspension of the solid material of the second cation exchange resin is buffered, agitated and suction filtered. Further dialysis and lyophilization yields low yields of a crude solid extract containing erythropoietin.

Initial attempts to isolate erythropoietin from urine yielded unstable, biologically inactive preparations of the hormone. U.S. Pat. No. 3,865,801 describes a method of stabilizing the biological activity of a crude substance containing erythropoietin recovered from urine. Apparently the presence of two enzyme activities, proteases and sialidases, acts to degrade the polypeptide and to remove the sialic acid terminal sugars from active erythropoietin. The patent discloses a method of removing enzyme activities from the preparation of erythropoietin by dissolving crude urinary erythropoietin in a phosphate-buffered-saline solution and adding sodium p-aminosalicylate. A solution of phenol, a phosphate buffer, and sodium p-aminosalicylate is equilibrated and combined with the feed solution. The resulting solution is extracted and dialyzed against a phosphate-buffered-saline solution. The crude preparation containing erythropoietin purportedly retains 90% of erythropoietin activity, and is stable.

Another method of purifying human erythropoietin from urine of patients with aplastic anemia is described by the applicant Goldwasser and his co-workers in Miyake, Kung, and Goldwasser, "Purification of Human Erythropoietin," *J. Biol. Chem.*, Vol. 252, No. 15 (Aug. 10, 1977), pp. 5558–5564. This seven-step procedure includes ion exchange chromatography, ethanol precipitation, gel filtration, and adsorption chromatography, and yields a crude erythropoietin preparation with a potency of 70,400 units/mg of protein in 21% yield. The purified hormone has a single electrophoretic component in polyacrylamide gels at pH 9, in the presence of sodium dodecyl sulfate at pH 7, and in the presence of Triton X-100 at pH 6. Two fractions of the same potency and molecular size, by sodium dodecyl sulfate gel electrophoresis, but differing slightly in mobility at pH 9, are obtained at the last step of fractionation.

Other techniques utilized to obtain purified erythropoietin involve immunological procedures. A polyclonal antibody directed against erythropoietin is developed by injecting an animal, preferably a rat or rabbit, with human erythropoietin. The injected human erythropoietin is recognized as a foreign antigenic substance by the immune system of the animal and elicits production of antibodies against the antigen. Differing cells responding to stimulation by the antigenic substance produce and release into circulation antibodies slightly different from those produced by other responding cells. The antibody activity remains in the serum of the animal when its blood is extracted. While unpurified serum or antibody preparations purified as a serum immunoglobulin G fraction may then be used in assays to detect and complex with human erythropoietin, the materials suffer from a major disadvantage. This serum antibody, composed of all the different antibodies produced by individual cells, is polyclonal in nature and will complex with components in crude extracts other than erythropoietin alone.

There exists, therefore, a substantial need in the art for a relatively simple method of obtaining large quantities of pure, biologically active erythropoietin from plasma or urine. There also exists a need for materials useful in the accurate quantitative detection of erythropoietin in human fluid samples.

BRIEF SUMMARY

The present invention provides a new rat-mouse hybridoma cell line ATCC CRL 8164, which provides as a component of the supernatant of its growth a highly specific monoclonal, anti-erythropoietin antibody, termed "Epoclonalan." Tumor cell line, ATCC CRL 8164, is on deposit at the American Type Culture Collection, 12301 Parklawn Drive, Rockville, Maryland 20852. According to the invention, Epoclonalan is employed in immunological procedures for the isolation of large quantities of pure, biologically active erythropoietin and in diagnostic immunoassays for the quantitative detection of erythropoietin in fluids of polycythemic, anemic or renal transplant patients. The antibody is also useful in verifying titers of erythropoietin produced by recombinant DNA techniques.

According to the present invention, a tumor cell line is produced using a standard immunological technique as described in Kohler, G., and C. Milstein, Nature (London) 256 (1975) 495-497; and Kohler, G., and C. Milstein, Eur. J. Imm. 6 (1976) 511-519. Briefly, lymphocytes removed from the spleen of male rats hyperimmunized with injections of crude human urinary erythropoietin are fused with a mouse myeloma cell line in the presence of a chemical fusogen. The supernatant from growth of each "hybridoma" cell culture is tested for the presence of the desired antibody activity. When such activity is found in the supernatant of one cell culture, it is cloned by limiting dilutions and the clones produced are individually assayed for supernatant activity. A selected hybridoma cell cloned to propagate cell line ATCC CRL 8164 produces an antibody in its growth supernatant which has highly specific anti-erythropoietin antibody action.

This monoclonal antibody, Epoclonalan, shows a specific attraction for human erythropoietin in fluids when it is employed in various immunological procedures including radioimmuno binding assays, and competitive binding assays. In immunological procedures to detect the presence of erythropoietin, Epoclonalan forms an immunoprecipitate with erythropoietin and a second antibody, which precipitate can be centrifuged from solution. Epoclonalan can therefore be utilized in immunological procedures for isolation and characterization of pure, biologically active erythropoietin as well as for the quantitative detection of erythropoietin in biological fluids such as whole blood, serum, cystic fluid, urine, and cerebrospinal fluid.

Other aspects and advantages of the present invention will become apparent upon consideration of the following detailed description.

DETAILED DESCRIPTION

In the procedure for production of cell line ATCC CRL 8164, ACI male rats (Lab Supply, Indianapolis, Indiana) were hyperimmunized to the hormone erythropoietin by inoculating the two-month-old rats intraperitoneally with 925 units (1.32 mg of protein) of crude human urinary erythropoietin, (purified according to the procedures described in Miyake, et al., J. Biol. Chem., supra) potency 700 units per mg protein, once each week for three weeks. The erythropoietin used for the initial injection was emulsified with an equal volume of complete Freund's adjuvant; and for all subsequent injections incomplete Freund's adjuvant was used. Fifty-seven days after the last injection, each rat was given a subcutaneous injection of 690 units (0.99 mg protein) of erythropoietin followed by a subcutaneous injection of 300 units (0.43 mg protein) of erythropoietin six days later. Anti-erythropoietin activity in the serum was monitored by immunoprecipitation of samples of serum using goat anti-rat immunoglobulin to precipitate pure $I^{125}$ labelled erythropoietin-antibody complexes.

Ten days after the last injection, lymphocytes derived from the spleens were removed from the rats (Davidson, W. F., and C. R. Parrish, Jr., J. Imm. Methods, 7, pp. 291-295 (1975)). $5 \times 10^7$ lymphocyte cells (immune donor spleen cells) were fused with $5 \times 10^6$ cells of the non-secreting mouse myeloma cell line SP2/0-Ag14 (Dr. Frank Fitch, University of Chicago) in the presence of the fusogen, polyethylene glycol according to the procedure of Kohler, G., and C. Milstein, Nature (London) 256 (1975) 495-497, and incubated in Dulbecco's medium with 20% fetal calf serum at 37° C. in a 5% $CO_2$ atmosphere. Selection of the SP2/0:rat spleen cell hybrids from the fusion (which also produces SP2/0:SP2/0 and rat spleen:rat spleen cell hybrids) was accomplished by centrifuging the cells 24 hours after fusion and culturing the fusion mixture in 96 well microtiter plates at a density of $2 \times 10^4$ myeloma cells per well in hypoxanthine/aminopterin/thymidine (HAT) medium (hybrid selection growth medium). The HAT medium prevented the SP2/0:SP2/0 cell hybrids from growing. The spleen:spleen cell hybrids generally died after two weeks in culture. Thus, the HAT medium allowed growth of only the SP2/0:rat spleen hybrid cells.

After cell growth in HAT medium for two weeks, the supernates of cultures were individually harvested and tested for the presence of antibody directed against erythropoietin by a binding assay described infra. Hybridoma cells that secreted antibody with binding activity were cloned by the limiting dilution method, transfer into a growth medium, Dulbecco's Modified Eagle's Medium with 20% fetal calf serum (Gibco Laboratories), in culture plates using irradiated ACI rat thymocytes as feeder cells. [Reed, L.C.M., "Methods in Enzymology," Vol. 58, pp. 152-164, W. B. Jakoby and I. H. Pastan, eds., New York: Academic Press, 1979).] The supernate of each culture was then re-tested for antibody activity and positive clones were transferred into growth medium in larger flasks.

Following these procedures, cell line ATCC CRL 8164 was found to produce a specific monoclonal anti-erythropoietin antibody in its supernate. Generation of Epoclonalan-containing supernate using ATCC CRL 8164 is accomplished by initially seeding the culture medium from hybridoma cells at $10^6$ cells/ml in serum-free Dulbecco's Modified Eagle's Medium (Gibco Laboratories) and incubating in a 5% $CO_2$—95% air atmosphere for approximately 48 hours.

Alternatively Epoclonalan can be obtained by the ascites method. In this procedure, $3 \times 10^6$ cells of ATCC CRL 8164 are injected into the peritoneal cavities of Nu/Nu immunologically nude mice (Harlan Sprague Dawley, Indianapolis, Indiana), which had received an injection of 0.25 milliliter of Pristane (Aldrich Chemical Co.). Pristane permits growth of tumor cells in an ascitic form within the peritoneal cavity. Within two weeks the ascitic tumor cells grow, the mouse is sacrificed, and the ascitic fluid containing monoclonal antibody is collected. The procedures for obtaining monoclonal antibody by the ascites method are described in Kenneth, R. H., T. J. McKearn and K. B. Bechtol (eds.), *Monoclonal Antibodies, Hydridomas: A New Dimension in Biological Analyses*, p. 403, New York: Plenum Press (1980).

Both the tissue culture medium and ascites fluid containing the monoclonal antibody Epoclonalan are then subjected to affinity chromatography, dialysis and precipitation techniques to purify the antibody. The supernatant medium, or ascites fluid, is centrifuged at 10,000×g for 30 minutes, at 4° C., and then passed through a column containing goat anti-rat immunoglobulin linked to Sepharose 4B in a concentration of 20 mg of protein/ml of beads. The rat-derived monoclonal antibody is thereby bound by affinity to the anti-rat immunoglobulin on the column, while other elements of the medium or fluid elute out of the column. The bound Epoclonalan immunoglobulin is then eluted from the column with 3 M NaSCN, pH 6.0. The antibody from the tissue culture supernate, after dialysis against 130 mM borate buffer, 75 mM NaCl, pH 8.3, is concentrated by precipitation with ammonium sulfate at 45% saturation at 24° C., dissolved in the same borate buffer at a concentration of 820 µg/ml and dialyzed against 1 liter of the same buffer with three changes over a period of 18 hours. The antibody in the peritoneal fluid of the nude mice was precipitated three times with ammonium sulfate at 45% saturation at 24° C. and dialyzed at a concentration of 8 mg of protein per milliliter of buffer. [*Methods in Immunology*, 3rd ed., pp. 245-255, J. S. Garvey, N. E. Cremer, D. H. Sussday, eds., Massachusetts: W. A. Benjamin, Inc. (1977).] These procedures result in the production of the monoclonal antibody Epoclonalan in the form of an immunoprecipitate.

Assays and tests to determine Epoclonalan's physiological characteristics have revealed that the antibody, proteinaceous in nature, shows under electrophoresis two major protein bands with molecular weights of 52,000 and 23,000, characteristic of the heavy and light chains of the IgG class of immunoglobulins. The monoclonal antibody binds $\alpha$, $\beta$ and asialo erythropoietin in labelled, inactive form and unlabelled, biologically active $\alpha$ and $\beta$ forms. The biological activity of the erythropoietin is not neutralized when the erythropoietin is bound to Epoclonalan.

The monoclonal anti-erythropoietin antibody, Epoclonalan, is advantageously employed in immunoassays devised to quantitatively detect erythropoietin in human fluids. Such an assay is the radioimmunoassay described in Fisher, et al., U.S. Pat. No. 4,254,095, which employs rabbit anti(human)-erythropoietin antiserum as a source of polyclonal antibody and an erythropoietin-conjugate as the labelled antigen. The basic principle of radioimmunoassay is the competition between labelled and unlabelled antigen for a fixed number of antibody binding sites. When increasing amounts of unlabelled antigen and a fixed amount of labelled antigen are reacted with a fixed and limiting amount of antibody, a decreasing amount of labelled antigen is bound to the antibody. The antibody-bound and free antigen may be separated by the double antibody technique and the percent labelled bound antigen determined by gamma counting. The relationship of bound labelled antigen to added non-labelled antigen is expressed as a standard curve and the amount of unlabelled antigen in the sample is determined.

Use of Epoclonalan as the antibody source, rather than the antiserum used in U.S. Pat. No. 4,254,095, in the antigen-antibody methodology permits the use of Protein A, a commercially available product, as the second antibody in the double antibody separation technique. Protein A binds specifically to the Fc region of human and animal immunoglobulins. Therefore, Protein A can replace the second antibody, which normally is specifically directed against the source of the antiserum. This is a desirable feature in the creation of an inexpensive, easily available assay for clinical diagnosis of abnormal amounts and/or activity of erythropoietin in such human body fluids as serum, urine, cerebrospinal fluid, milk, and cystic fluid. Several assays in which Epoclonalan may replace serum polyclonal antibody are described in Sherwood, J. B., and E. Goldwasser, "A Radioimmunoassay for Erythropoietin," *Blood*, Vol. 54, No. 4 (October, 1979), pp. 885-893; and Goldwasser, E., J. F. Eliason, and D. Sikkema "An Assay for Erythropoietin in Vitro at the Milliunit Level," *Endocrinology*, Vol. 97, No. 2 (August 1975), pp. 315-323.

Epoclonalan also has significant use in isolating, from human fluids, large quantities of pure erythropoietin. Use of the antibody in immuno-affinity methodologies, such as chromatography columns or other solid state modalities to which the antibody is bound, would enable extraction of the hormone from a fluid sample contacted with the bound antibody. Extraction of large quantities of hormone would be advantageous to intensive study of the hormone and its mechanism and in treatment of individuals with deficient erythropoiesis mechanisms, i.e., certain types of anemia.

In addition, Epoclonalan would be useful in recombinant DNA procedures wherein the structural gene for the hormone is recombined with bacterial, yeast or cultured mammalian cells and these host cells are used to express that gene in the form of an active protein. Epoclonalan can be used as a probe to determine if biologically active erythropoietin is being properly synthesized by such an expression system.

The antibody has further potential application to detection of erythropoietin-responsive and synthesizing cells in individuals undergoing bone marrow transplantation. Additionally, Epoclonalan in an immunological complex with glycosylated erythropoietin may enable the carbohydrate-free hormone to survive longer in vivo for treatment of defects in erythropoietic systems.

The following examples illustrate immunological assays using the monoclonal antibody of the present invention and, more specifically, relate to assays evidencing Epoclonalan's specificity for labelled and unlabelled erythropoietin, its ability to recover erythropoietin in large quantities, and determination of its physiological and chemical characteristics.

EXAMPLE 1

Recovery of Erythropoietin from Urine

An immobilized, insoluble derivative of the monoclonal antibody is prepared by covalently linking the antibody to an agarose matrix in a column. Human urine containing crude erythropoietin is brought into contact with the antibody-linked matrix under conditions of ionic strength and pH that will maximize binding of erythropoietin to the antibody. Because of the specificity of the monoclonal antibody, little to no contaminating substances are bound to the matrix. The matrix is washed to remove unbound and loosely adherent proteins. Erythropoietin is then eluted from the matrix by 3 M NaSCN at pH 6.0.

Yields of approximately 50% are obtained in the eluate with a potency of 30,000 to 40,000 units per milligram of protein.

EXAMPLE 2

Radioimmunobinding Assay for Anti-Erythropoietin Activity

A radioimmunobinding assay was devised to detect the anti-erythropoietin activity of Epoclonalan produced by hybridoma cell line ATCC CRL 8164.

The procedures for the assay were the following: Hybridoma culture medium containing Epoclonalan was diluted more than 7 fold with 7 mM borate buffer, 150 mM NaCl, pH 8.3 (BBS). A 25 μl aliquot of this diluted medium containing the monoclonal antibody was added to 100 μl of BBS containing 100,000 counts/-minute of eryrhropoietin labelled with radioactive iodine ($^{125}$I) (0.2 pmoles) and 2% non-immune rat serum. The reaction mixture is incubated for 2 hours at 37° C. during which the Epoclonalan in the culture medium and the labelled erythropoietin form antigen-antibody complexes in microtiter plates. 50 μl of goat anti-rat immunoglobulin (Gibco Laboratories) is then added as the second antibody to precipitate immune complexes of goat anti-rat antibody: Epoclonalan (rat-derived)-:erythropoietin. The $^{125}$I-erythropoietin:Epoclonalan:-goat-anti-rat antibody immunoprecipitates in the microtiter plates are separated from free labelled $^{125}$-I erythropoietin in the solution by centrifugation at 2000×g for 10 minutes, and washing with 100 μl of BBS. The immunoprecipitates are then dissolved in 50 μl of 1 M NaOH and the radioactivity of the $^{125}$I erythropoietin bound to Epoclonalan is counted.

The same procedure was followed using 25 μl aliquots of undiluted hybridoma culture medium, and undiluted monoclonal antibody derived from the peritoneal fluid of mice (ascites fluid), and various dilutions of both sources of Epoclonalan. Additionally, immune serum (polyclonal antibody) taken from the rat when the spleen was removed was subjected to this procedure for use as a positive control.

For undiluted ascited fluid antibody and for less than 7-fold dilutions of ascites fluid antibody, the amount of monoclonal antibody was too great to be completely precipitated by the goat-anti-rat immunoglobulin. The procedures for the assay were modified as follows for those antibody sources: Following the 2 hours of incubation at 37° C. as described above, 200 μl of rabbit anti-rat serum (rather than 50 μl of goat-anti-rat) s added as the second antibody. This mixture is incubated for an additional 30 minutes at 37° C. A 400 μl aliquot of 10% Staph A (Staphylococcus aureus, heat-killed and formalin-mixed, The Enzyme Center, Boston, Mass.) is added to each reaction mixture and the samples are mixed, then centrifuged at 15,000×g for 3 minutes The immunoprecipitate is washed with 1.0 ml of BBS, centrifuged and radioactivity counted. Non-immune rat serum controls are run to correct for nonspecific binding.

Positive binding of these Epoclonalan-containing cultures and fluids was indicated by radioactivity counts higher than the controls.

The results of the radioimmunobinding assays demonstrate that hybridoma culture medium immunoglobulin shows a small but detectable antibody activity even when diluted a thousand fold. As shown in Table I, the monoclonal antibody bound a maximum of 44% of the trichloroacetic acid precipitable radioactivity. The serum from the immunized rat (polyclonal antibody) bound more erythropoietin when undiluted but at the highest dilution was about equivalent to the monoclonal antibody.

TABLE I

| | % $^{125}$I-erythropoietin Bound | |
|---|---|---|
| Dilutions | Antibody | Serum |
| $10^0$ | 44.0% | 68.0% |
| $10^{-1}$ | 20.0% | 44.0% |
| $10^{-2}$ | 5.0% | 17.0% |
| $10^{-3}$ | 2.5% | 3.0% |

Additionally, the assay revealed that the monoclonal antibody does not bind all of the labelled erythropoietin in the assay. Decreasing the amount of labelled erythropoietin in the binding assay did not result in the binding of labelled antigen beyond the 50% level. The 2 hour, 37° C., incubation of the monoclonal antibody with $^{125}$I-erythropoietin was sufficient for maximum binding, since no further binding was detected at longer times or with incubation periods of up to 68 hours at 4° C. Precipitation with goat anti-rat immunoglobulin did not result in complete removal of the immune complex, but a combination of Staph A and rabbit anti-rat immunoglobulin did, however, precipitate all of the $^{125}$I-erythropoietin:Epoclonalan:anti-rat antibody complex and unbound Epoclonalan. The labelled erythropoietin that remained in solution was not capable of being bound by either the immune serum or the monoclonal antibody.

When binding assays were performed with both the α and β forms of erythropoietin, the results revealed that Epoclonalan binds both the α and β forms to the same extent as did the rat immune serum. A preparation of the iodinated α asialo form of erythropoietin was also subjected to a binding assay and revealed that an amount equal to the native α hormone was bound to the monoclonal antibody, although the immune rat serum binds significantly more native than asialo erythropoietin. Table II shows the comparative binding assay results. The percent of total counts bound have been adjusted for the nonspecific binding (1%) observed with 2% normal rat serum. The polyspecific immune serum was tested as a tenfold dilution.

TABLE II

Reactivity of Monoclonal Antibody Epoclonalan with the α and β Forms of Erythropoietin

| | Percent Bound | |
|---|---|---|
| Preparation | Monoclonal Antibody | Immune Serum (Polyclonal Antibody) |
| α erythropoietin | 33% | 43% |
| β erythropoietin | 34% | 39% |
| asialo α erythropoietin | 33% | 14% |

These data indicate that Epoclonalan binding of erythropoietin does not distinguish between the two forms, α and β, having somewhat different carbohydrate structures. Nor does Epoclonalan distinguish between intact oligosaccharide chains and chains devoid of terminal sialic acids. It thus appears that the significant antigenic determinant of erythropoietin recognized by Epoclonalan is within the polypeptide portion.

EXAMPLE 3

Determination of Physiological and Chemical Characteristics of Epoclonalan

I. By Electrophoretic Procedures

A. To determine the number and molecular weight of the polypeptide constituents of the protein Epoclonalan, one-dimensional sodium dodecylsulfate (SDS) electrophoresis was carried out in 10% and 12% polyacrylamide gels using a discontinuous buffer system.

The supernatant medium taken from hybridoma clone ATCC CRL 8164, grown in serum free Dulbecco's medium, was electrophoresed in 1% SDS. The detergent dissociates the protein Epoclonalan into subunits and completely unfolds each polypeptide chain to form a long, rodlike SDS-polypeptide complex. In this complex the polypeptide chain is coated with a layer of SDS molecules in such a way that their hydrocarbon chains are in tight hydrophobic association with the polypeptide chain and the charged sulfate groups of the detergent are exposed to the aqueous medium. Such complexes contain a constant ratio of SDS to protein (about 1.4:1 by weight) and differ only in mass. When an SDS-treated single-chain protein is subjected to electrophoresis in a gel containing SDS, its rate of migration is determined primarily by the mass of the SDS-polypeptide particle. The electric field simply supplies the driving force for the molecular sieving.

Two major protein bands migrated with an apparent molecular weight of 52,000 and 23,000, characteristic of the heavy and light chains of the IgG class of immunoglobulin.

B. The specificity of the monoclonal antibody Epoclonalan for erythropoietin was tested by electrophoretic procedures using pure preparations of erythropoietin.

The immunoprecipitates containing pure $^{125}$I-erythropoietin and either monoclonal antibody or the polyclonal rat immune serum were dissolved in 50 μl of 0.125 M tris-HCl, pH 6.8 containing 1% SDS and 1% β-mercaptoethanol and heated for 5 minutes at 100° C. This treatment caused the dissociation of erythropoietin from the immunoglobulin. After the addition of 12% glycerol and 0.005% bromphenol blue, these dissociated immunoprecipitates, an $^{125}$I-erythropoietin control, a normal rat serum control, and the remaining supernatants of the immunoprecipitates were put on the polyacrylamide gel in adjacent lanes. The samples were electrophoresed for 18 hours at room temperature at 50 volts/cm and 15 mamps. The gels were stained with 0.06% Coomassie Blue R in 25% isopropanol, 10% acetic acid, then destained in 10% isopropanol, 10% acetic acid and dried. The gels were then autoradiographed at −70° C. using Kodak X-Omat R film for 12 to 20 hours.

The autoradiogram of this gel showed that both the monoclonal antibody and the immune serum bind pure $^{125}$I-erythropoietin. The normal rat serum control showed no significant binding. Frequently two very minor autoradiographic bands are revealed in addition to the major Epoclonalan band in preparations of the purified Epoclonalan control and in the immunoprecipitates when the pure $^{125}$I-erythropoietin-monoclonal antibody (or immune serum) complex has been dissociated. These minor bands are probably aggregates of erythropoietin which occur under certain conditions.

C. For further characterization of the monoclonal antibody specificity, a labelled crude preparation of erythropoietin was used following the procedures in Part B above. Immune complexes were formed with either the monoclonal antibody or the polyclonal rat immune serum and precipitated with goat anti-rat immunoglobulin. The immunoprecipitates were dissolved, and the bound proteins were dissociated from the immunoglobulin with 1% SDS and 1% β-mercaptoethanol. The dissociated iodinated crude immunoprecipitates, erythropoietin, and a normal rat serum control were electrophoresed in adjacent lanes.

The autoradiogram of this gel showed essentially only one labelled protein band precipitated out of the mixture by the monoclonal antibody, while several protein bands precipitated out of the mixture by the polyspecific immune antiserum.

These results indicate that the monoclonal antibody Epoclonalan reacts only with erythropoietin when incubated with the mixture of proteins and glycoproteins found in concentrates of human urine. The polyspecific immune antiserum, however, reacts with not only erythropoietin but with several of the proteins and glycoproteins contained in urine as well.

II. By High Pressure Liquid Chromatography

Erythropoietin was subjected to high pressure liquid chromatography to demonstrate that erythropoietin is bound to the monoclonal antibody and to determine whether any unbound fraction might consist of fragments arising from protein degradation.

100 μl of a solution containing 27,000 cpm of $^{125}$I-erythropoietin in 0.15 M ammonium acetate, pH 7.0, containing 0.01% polyethylene glycol-6000 was added to a 50 cm TSK G-3000 sizing column equilibrated with 0.15 M ammonium acetate, pH 7.0, containing 0.01% polyethylene glycol-6000 and run at 300 psi and 0.7 ml/minute. Fractions (0.3 ml) were collected and $^{125}$I counted. The pure $^{125}$I-erythropoietin elutes as one sharp, radioactive peak.

The same conditions were used to analyze 53 μg of peritoneal fluid protein from the nude mice previously injected with the hybridoma cell line ATCC CRL 8164. The elution profile of the peritoneal fluid containing the monoclonal antibody Epoclonalan shows two absorbance peaks. The second peak has an approximate molecular weight of about 75,000.

When 20 μl of the peritoneal fluid containing Epoclonalan was incubated for 2 hours at 37° C. with 43,000 cpm of $^{125}$I-erythropoietin in BBS and an aliquot chromatographed, the elution profile had three radioactive peaks. The first radioactive peak to be eluted was $^{125}$I-erythropoietin bound to the protein found in Peak I of the peritoneal fluid. The second radioactive peak is $^{125}$I-erythropoietin bound to peak II of the peritoneal fluid. The third peak eluted at the same volume as that of the $^{125}$I-erythropoietin control and is unbound erythropoietin.

When the two protein peaks which eluted from the peritoneal fluid chromatograph were incubated separately with $^{125}$I-erythropoietin, they bound approximately the same amount of $^{125}$I-erythropoietin per gram of protein. The smaller molecular weight protein in the peritoneal fluid is considered to be a complex composed of one heavy and one light chain which retains its antigen recognizing site. The large molecular weight protein is the intact gamma globulin Epoclonalan consisting of two heavy and two light chains.

III. By Competitive Radioimmunoassay

Attempts to radiolabel erythropoietin result in the inactivation of its biological activity. To determine whether the monoclonal antibody Epoclonalan binds unlabelled, biologically active erythropoietin, a competitive radioimmunoassay was conducted.

An antibody concentration which binds 15% of the $^{125}$I-erythropoietin was used with increasing amounts of the hormone (70,000 units/mg of protein). 100 µl of a mixture containing 100,000 counts/minute of $^{125}$I-erythropoietin, 2% normal rat serum, varying amounts of competing, unlabelled erythropoietin, ranging from 0.13 to 17.3 µg per tube, and an erythropoietin diluent (0.15 M NaCl, 0.1% bovine serum albumin, 10 mM CaCl$_2$) used to keep the volume constant were added to 25 µl aliquots of Epoclonalan diluted with BBS. The incubation and the processing of the immunoprecipitates were carried out as described above in Example 2, the description of the radioimmunobinding assay.

The monoclonal antibody Epoclonalan does, indeed, bind biologically active erythropoietin. An unusually large amount of unlabelled erythropoietin ($2.5 \times 10^3$ excess) is necessary to compete for 50% of the monoclonal antibody binding sites when compared to the polyclonal antibody obtained from rabbits. This must be due to the high affinity of binding between the monoclonal antibody and the $^{125}$I-erythropoietin. Table III shows the results of the competitive radioimmunoassay.

TABLE III

| Unlabelled Erythropoietin (µg) in Assay Mixture | Fraction $^{125}$I Erythropoietin Bound by Epoclonalan |
|---|---|
| 0.5 | 0.91 |
| 1.0 | 0.90 |
| 5.0 | 0.68 |
| 10.0 | 0.45 |

This ability of the monoclonal antibody, Epoclonalan, to bind native, biologically active erythropoietin as well as the radioactive iodine-labelled inactive forms, indicates that Epoclonalan is an ideal diagnostic agent.

IV. By an Erythropoietin Assay

The ability of the monoclonal antibody Epoclonalan to neutralize the biological activity of erythropoietin was tested by assaying the erythropoietin:Epoclonalan immune complex for biological activity in rat bone marrow cell cultures.

Microfuge tubes, previously coated with polyethylene glycol 20,000, containing 48 munits of erythropoietin (70,000 units/mg of protein) and increasing amounts of peritoneal fluid containing monoclonal antibody Epoclonalan from 9 to 514 µg and phosphate buffered saline (PBS) in a final volume of 80 µl were incubated for 2 hours at 37° C. A control tube containing 48 munits of erythropoietin in PBS with a final volume of 80 µl was also incubated for 2 hours at 37° C. Six replicate cultures of rat bone marrow cells were incubated with 10 µl of sample for 20 hours at 37° C. before the addition of $^{59}$Fe. A standard curve of 0, 4, 6, and 8 munits of erythropoietin was also run.

Erythropoietin activity was measured by the amounts of radio-labelled iron taken up by the bone marrow cells as they synthesize hemoglobin and mature into red blood cells.

The incubation of 48 munits of pure erythropoietin with 0 to 514 µg of Epoclonalan protein from the peritoneal fluid resulted in no detectable inactivation of erythropoietin activity, thus indicating that the soluble complex of Epoclonalan-erythropoietin is fully active in its effect on target cells of rat bone marrow.

The foregoing examples and detailed description are provided for clarity of understanding only, and no unnecessary limitations should be understood therefrom, as modifications will be obvious to those skilled in the art.

What is claimed is:

1. A novel hybridoma cell line, ATCC No. CRL 8164, that produces a monoclonal antibody having specific binding affinity to and lacking neutralization of erythropoietin.

2. A monoclonal antibody, Epoclonalan, produced by hybridoma cell line ATCC No. CRL 8164 and having selective binding affinity to and lacking neutralization of erythropoietin.

3. In an immunological procedure for the isolation of erythropoietin wherein:
   (1) a fluid sample containing erythropoietin is contacted with an antibody specific for erythropoietin,
   (2) the erythropoietin in the fluid is bound by said antibody in a selective immunological reaction resulting in the formation of an antigen-antibody complex,
   (3) said complex is separated from said fluid, and
   (4) the erythropoietin is separated from said complex,
   the improvement comprising: employing as said specific antibody a monoclonal antibody, Epoclonalan, produced by hybridoma cell line ATCC No. CRL 8164 and having selective binding affinity to and lacking neutralization of erythropoietin.

4. The improvement of claim 3 wherein said fluid is human fluid.

5. The improvement of claim 4 wherein said fluid is a member of the group comprising: whole blood, serum, cystic fluid, urine, cerebrospinal fluid.

6. The improvement of claim 3 wherein said immunological procedure is selected from the group consisting of affinity chromatography, and ELISA.

7. In an immunological procedure for the quantitative detection of erythropoietin wherein:
   (1) a fluid sample containing erythropoietin is contacted with an antibody specific for erythropoietin,
   (2) the erythropoietin in the fluid is bound by said antibody in a selective immunological reaction resulting in the formation of an antigen-antibody complex,
   (3) said amount of erythropoietin in said sample is detectable by the amount of complex formed, and
   the improvement comprising: employing as said specific antibody a monoclonal antibody, Epoclonalan, produced by hybridoma cell line ATCC No. CRL 8164 and having selective binding affinity to and lacking neutralization of erythropoietin.

8. The improvement of claim 7 wherein said fluid is human fluid.

9. The improvement of claim 8 wherein said fluid is a member of the group comprising: whole blood, serum, cystic fluid, urine, cerebrospinal fluid.

10. The improvement of claim 7 wherein said immunological procedure is a radioimmunobinding assay.

* * * * *

UNITED STATES PATENT AND TRADEMARK OFFICE
CERTIFICATE OF CORRECTION

PATENT NO. : 4,558,005

DATED : December 10, 1985

INVENTOR(S) : EUGENE GOLDWASSER, CLIFFORD KAVINSKY & TANIA L. WEISS

It is certified that error appears in the above-identified patent and that said Letters Patent is hereby corrected as shown below:

Column 7, line 53, change "s" to --is--.

Column 7, line 40 and 41, change "pertoneal" to --peritoneal--.

Column 7, line 60, insert a --.-- before "The".

Signed and Sealed this

Eighteenth Day of November, 1986

Attest:

DONALD J. QUIGG

*Attesting Officer*  *Commissioner of Patents and Trademarks*